United States Patent [19]
Shah

[11] Patent Number: 5,942,243
[45] Date of Patent: Aug. 24, 1999

[54] MUCOADHESIVE COMPOSITIONS FOR ADMINISTRATION OF BIOLOGICALLY ACTIVE AGENTS TO ANIMAL TISSUE

[75] Inventor: Kishore R. Shah, Bridgewater, N.J.

[73] Assignee: Polytherapeutics, Inc., Brdigewater, N.J.

[21] Appl. No.: 09/076,216

[22] Filed: May 12, 1998

Related U.S. Application Data

[63] Continuation-in-part of application No. 08/746,327, Nov. 12, 1996, Pat. No. 5,814,329.
[51] Int. Cl.$^6$ .............................. A61K 47/32; A61K 9/02
[52] U.S. Cl. ............................................. 424/434; 424/435
[58] Field of Search ...................... 424/435, 434

[56] References Cited

U.S. PATENT DOCUMENTS

| | | | |
|---|---|---|---|
| 3,598,122 | 8/1971 | Zaffaroni | 128/268 |
| 4,994,322 | 2/1991 | Delgado et al. | 428/343 |
| 5,104,952 | 4/1992 | Babu | 526/279 |
| 5,116,910 | 5/1992 | Tone et al. | 525/244 |
| 5,179,158 | 1/1993 | Azuma et al. | 524/748 |
| 5,417,983 | 5/1995 | Nagase et al. | 424/487 |

OTHER PUBLICATIONS

E. Arca et al. Release of . . . Media Int.J. Pol. Anal.—Character. 1995 vol.2, pp. 31–41 Nov. 1994.

*Primary Examiner*—Peter F. Kulkosky
*Attorney, Agent, or Firm*—Hoffmann & Baron, LLP

[57] ABSTRACT

This invention pertains to mucoadhesive compositions for the delivery of pharmacologically active agents, and to polymeric formulations that allow for a prolonged, sustained release of the active agents. More specically the invention pertains to compositions for the delivery of drugs to mucosal tissue, said composition comprising a drug or a plurality of drugs to be delivered and a thermoplastic graft copolymer, said graft copolymer being the reaction product of a polystyrene macromonomer having an ethylenically unsaturated functional group, and at least one acidic hydrophilic monomer having an ethylenically unsaturated functional group.

21 Claims, 1 Drawing Sheet

MUCOADHESIVE COMPOSITIONS FOR ADMINISTRATION OF BIOLOGICALLY ACTIVE AGENTS TO ANIMAL TISSUE

CROSS-REFERENCE

The present application is a continuation-in-part of application Ser. No. 08/746,327, now U.S. Pat. No. 5,814,329 entitled "Hydrophilic Polystyrene Graft Copolymer for Intravaginal Administration of Pharmacologically Active Agents", filed Nov. 12, 1996.

FIELD OF THE INVENTION

This invention pertains to mucoadhesive compositions for sustained release of biologically active agents to mucosal tissue.

BACKGROUND OF THE INVENTION

Controlled release of a biologically active agents to a mucosal membrane improves therapeutic efficacy, safety, and patient compliance. Oral drug administration is associated with two phenomina, namely, 1) the first pass hepatic metabolism, and 2) systemic dilution. Mucosal drug delivery avoids the hepatic first pass metabolism and prevents systemic dilution of the drug, resulting in greater local bioavailability of a drug. Because mucosal drug delivery requires much lower amounts of the drug than oral administration, it minimizes the side effects of systemic drug circulation. Compared to oral drug administration, mucosal delivery also reduces the burden on the liver and other organs. Mucosal drug delivery can be used to provide therapeutic effectiveness proximal to the site of delivery, e.g. vaginal delivery of clotrimazole or miconazole nitrate for the treatment of vaginal yeast and fungal infections. However, delivery to a mucosal membrane also delivers drug to the systemic circulation, and can be used to make an active agent available for pharmacological effectiveness at another site or organ in the body. An example of such distal delivery is absorption of a cardiovascular drug through either a nasal or buccal mucosa.

Mucosal sites in the body include the cul-de-sac of the eye, buccal cavity, nose, rectum, vagina, periodontal pocket, intestines and colon. Due to natural eliminating or cleansing mechanisms of mucosal tissues, conventional dosage forms are not retained at the application site for any significant length of time. For example, drops of medications instilled in the cul-de-sac of the eye are easily eliminated; first, by overflowing, and subsequently, by drainage through puncta. Conventional vaginal dosage forms such as creams, ointments, suppositories, etc, are rapidly removed by self cleansing action of the vaginal tract.

For these and other reasons it is advantageous to have materials which exhibit adhesion to mucosal tissues, to administer one or more drugs or active agents over a period of time. Materials having controlled release capability are particularly desirable, and the use of sustained release mucoadhesives has received a significant degree of attention.

J. R. Robinson (U.S. Pat. No. 4,615,697) provides a good review of the various controlled release polymeric compositions used in mucosal drug delivery. The patent claims a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application.

Other approaches involving mucoadhesives which are the combination of hydrophilic and hydrophobic materials, are known. Orahesive® from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present invention produce an insoluble copolymer.

U.S. Pat. No. 4,948,580 describes a bioadhesive oral drug delivery system. The composition, includes a freeze-dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 discloses paste-like preparations comprising (A) a paste-like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water-in-oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material.

All the above compositions are physical mixtures, therefore they are more prone to break down and less likely to attain a long residence time. While their hydrophilic and hydrophobic components have some utility in drug delivery, using the hydrophilic and hydrophobic domains in the copolymers of the present invention make it is far easier to incorporate drugs within, and to formulate, dosage forms. Further, the compositions of the present invention do not break down upon hydration.

SUMMARY OF THE INVENTION

The present invention pertains to polymeric mucoadhesive compositions consisting essentially of a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group.

The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%.

Compositions containing the copolymers gradually hydrate by sorption of tissue fluids at the application site to yielding a very soft jelly like mass exhibiting adhesion to the mucosal surface. During the period of time the composition is adhered to the mucosal surface it provides sustained release of the pharmacologically active agent, which is absorbed by the mucosal tissue.

Mucoadhesivity of the compositions of this invention is, to a large extent, produced by the hydrophilic acidic monomers of the chain in the polystyrene graft copolymer. The acidic monomers include, but are not limited to, acrylic and methacrylic acids, 2-acrylamido-2-methyl-propane sulfonic acid, 2-sulfoethyl methacrylate, and vinyl phosphonic acid. Other copolymerizable monomers include, but are not limited to N,N-dimethylacrylamide, glyceryl methacrylate, polyethylene glycol monomethacrylate, etc.

The compositions of the present invention may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition. The dosage forms of the compositions of this invention can be prepared by conventional methods.

The various pharmaceutically active agents that may be used include drugs for systemic treatment of conditions as well as local treatment of conditions. Various treatments include drugs for neurological conditions, cardiovascular conditions, inflammatory diseases, pain relief, anticancer drugs, microbial infections, prevention of conception and the like. Peptide and protein drugs are specialty suitable for delivery via the mucosal route, because they are readily destroyed through the gastrointestinal tract when administered orally.

It is an object of the present invention to provide a controlled release polymeric composition for one or more biologically or pharmacologically active agents. Another object of the present invention is to provide a pharmaceutical dosage form which is water swellable but water insoluble. The dosage form can easily be formulated as user friendly articles such as powders, capsules, suppositories, ointments, films, laminates, tablets, solutions, dispersions and the like. In addition, the dosage form may be in a dehydrated state, or plasticized with a suitable plasticizer, or in a partially hydrated state.

A further object of this invention is to provide a pharmaceutical dosage form which exhibits adhesion to the mucous surfaces of animal tissues, but no local side effects or toxicity. Various mucosal sites in the body, to which the compositions of this invention may be applied, include cul-de-sac of the eye, oral mucosa, nose, rectum, vagina, periodontal pocket, intestines and colon.

Another object of the present invention is to provide a composition which is at once both convenient to formulate with a biologically, active agent and economical to manufacture.

The invention also envisions a method of treatment by application of the controlled release composition to a mucosal tissue. The application of the composition to the mucosa of the gastrointestinal tract may be carried out by swallowing the composition.

DETAILED DESCRIPTION OF THE INVENTION

The present invention is directed to a mucoadhesive controlled release pharmaceutical dosage composition, comprising of a hydrogel forming polystyrene graft copolymer and one or more pharmacologically active agents and methods of their use. For the purpose of this invention the terms controlled release and sustained release are used interchangeably to indicate a slow release of the active agent over an extended period of time. The principal drug delivery vehicle of the dosage form of the present application is a thermoplastic graft copolymer. The mucoadhesive composition may also optionally contain other polymeric materials, plasticizers, and other pharmaceutically acceptable excipients in amounts that do not cause deleterious effect upon mucoadhesivity of the composition.

Figure 1:
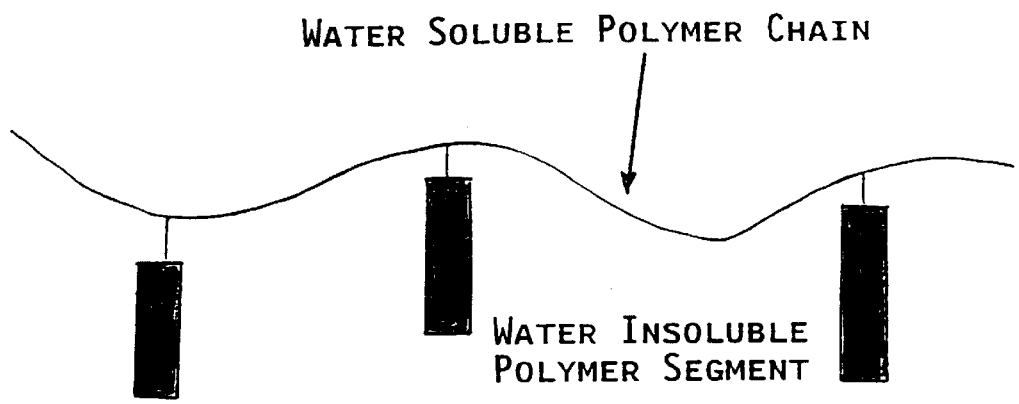
FIG. 1 is a schematic diagram of the arrangement of the water soluble main chain and the water insoluble polymer segments of the hydrophilic/hydrophobic graft copolymer of the present invention.
Figure 2:
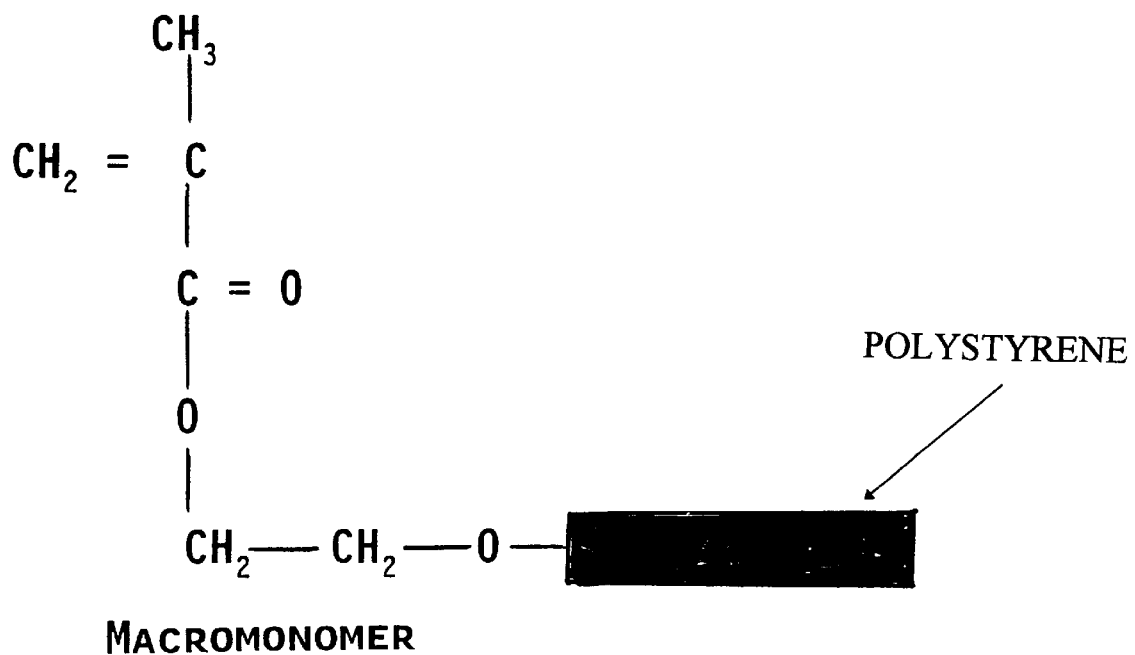
FIG. 2 is a schematic structure of the polystyrene macromonomer used in the compositions of the present invention.

The graft copolymer suitable for use in this invention has a hydrophilic polymeric main chain and a hydrophobic polymeric side chain (FIG. 1). The main chain is comprised of monomeric units having acidic groups and optionally neutral monomeric units. The preferred hydrophobic side chain moiety is polystyrene. The graft copolymer is prepared by free radical initiated polymerization of a polystyrene macromonomer having an ethylenically, unsaturated functional group (FIG. 2) with the acidic and neutral hydrophilic comonomers. The acidic comonomers suitable for preparation of the graft copolymer include acrylic acid, methacrylic acid, itaconic acid, 2-acrylamido-2-methyl-propane sulfonic acid, and 2-sulfoethyl methacrylate. The neutral comonomers of the main chain may include acrylamide, methacrylamide, 2-hydroxyethyl methacrylate, N,N-dimethylacrylamide, polyethylene glycol monomethacrylate, and glyceryl methacrylate. The method of preparation of the graft copolymer for use in this invention is analogous to that for poly(N,N-dimethylacrylamide-g-styrene) as disclosed in R. Milkovich, et al., U.S. Pat. No. 4,085,168, which is incorporated herein by reference.

The monomeric moieties of the graft copolymer are selected to perform the needed functions. The acidic and neutral hydrophilic monomeric units provide the hydrophilicity to absorb aqueous fluids, whereas the polystyrene graft chains contribute to the integrity and water insolubility of the copolymer, thus resulting in a water swollen but insoluble jelly like mass in the biological environment. The acidic functionality of the copolymer, in addition, contributes to adhesion to the mucosal surfaces so as to attain the necessary residence time of the gel. Release of the pharmacological agent from the swollen gel occurs gradually, by a process of diffusion. The hydrophilic neutral comonomer contributes to modification of the hydrophilicity and polarity of the graft copolymer for optimizing solubility of the pharmacological agents in it. The relative proportions of the three types of monomers may vary within certain limits. The proportion of polystyrene macromonomer may vary from about 1 to about 20 percent by weight, optionally from 1 to 10 percent by weight, and preferably, from 1 to 5 percent by weight, based on the total weight of the copolymer. The ethylenically unsaturated monomer containing acidic groups may vary from 10 to 90 percent by weight of the copolymer. Finally, the neutral hydrophilic monomer may vary from 0 to 89 percent by weight of the copolymer.

The graft copolymer for use in this invention exhibits microphase separation with a hydrophilic/hydrophobic domain system. The morphology of the graft copolymer is characterized by a hydrophilic continuous phase and a hydrophobic dispersed phase, which prevents the continuous phase from dissolving in water. Thus, when the graft copolymer is placed in an aqueous environment, it absorbs water and swells to an equilibrium volume, but does not dissolve in water. More specifically, the graft copolymer has an equilibrium water content, defined as the percentage by weight of water absorbed, based or the weight of the fully hydrated sample, of greater than 90%, and typically greater than 95%. Such graft copolymers are thermoplastic. Accordingly, they are soluble in conventional organic solvents and soften or melt upon the application of heat. Thus, the hydrogel forming graft copolymers of the present invention are distinguished from thermosetting polymers such as mucoadhesive hydrogels (J. R. Robinson, U.S. Pat. No. 4,615,697), which are insoluble in organic solvents and do not melt upon heating, because they are covalently crosslinked.

The graft copolymers for use in the present invention may be prepared separately, purified, and then formulated with the pharmacological agent and other excipients by either solution mixing/casting or melt mixing process. For example, a graft copolymer of N,N-dimethylamide, acrylic acid and polystyrene macromonomer may be prepared by free radical initiated solution polymerization. The starting materials are reacted in the presence of a polymerization solvent, such as ethyl acetate, ethanol, methyl ethyl ketone, acetone, tetrahydrofuran, mixtures thereof and the like, and a polymerization initiator (e.g. azobisisobutyronitrile) at a reaction temperature in the range of up to 80° C. The resulting solution containing the copolymer is then optionally purified to remove unreached monomer and other impurities. For example, the copolymer solution may be precipitated with a nonsolvent, such as diethyl ether, at a weight ratio of about 1:4. The resulting precipitated copolymer is separated, washed with excess non-solvent, and dried. The advantage of this process is that the pharmacological agent is not subject to chemically reactive species during the polymerization process as would be the case for thermosetting polymers.

Blending compatible water soluble polymers with the graft copolymer increases its equilibrium hydration capacity. Compatible water soluble polymers suitable for blending with the graft copolymer include, but are not limited to, poly(N-vinyl 2-pyrrolidone) and poly(N,N-dimethylacrylamide). The proportion of the water soluble polymer used in blending may vary from 0 to 75 percent by weight, based on the combined weights of the water soluble polymer and the graft copolymer.

Polyethylene glycol having a molecular weight of about 300 to 1500, preferably 400 to 600, can be used as a water soluble plasticizer for the graft copolymer to prepare a vaginal drug delivery dosage form. Alternatively, glycerine may also be used as a water soluble plasticizer. The proportion of the water soluble plasticizer in the dosage form may vary from about 10 to 50, preferably 20 to 40, percent by weight of the dosage form.

For the purpose of this application the active drug delivery vehicle consists essentially of the thermoplastic graft copolymer, by which is meant that although ingredients such as water, water soluble or water swellable polymers, and adjuvants, such as plasticizer, and diluents, such as solvents can be present, other ingredients that substantially and detrimentally alter the basic and novel characteristics of the drug delivery vehicle are absent.

Some of the pharmacological agents suitable for use in this invention include compounds for intravaginal administration. A few such examples are as follows:

Miconazole nitrate and clotrimazole are two suitable antifungal agents for the treatment of vaginal yeast (Candida) infection. The concentration of clotrimazole in the dosage form can vary from 1 to 10 percent by weight, based on the total weight of the dosage form. The polymeric hydrogel forming dosage form provides the benefits of sustained release of the dosage form over a prolonged period of time thus increasing the therapeutic effectiveness and patient compliance. The currently marketed products are creams which essentially dump the active agent at the site of application reducing the duration of therapeutic effectiveness. The hydrogel dosage form has an added benefit in that it does not contain some of the inactive ingredients present in the cream products, such as preservatives and surfactants, which may be potentially irritating to body tissues.

Nonoxynol-9, which is one of the major spermicidal agents used in the marketed spermicidal contraceptive products, may be incorporated in to the hydrogel forming dosage form. The concentration of nonoxynol-9 may vary from 10 to 40 percent by weight, based on the total weight of the dosage form. The currently available products are effective for only a short period of time (approximately 1 hour). Sustained release of nonoxynol-9 from the hydrogel forming dosage form can provide spermicidal activity for a period of greater than 8 hours. Greatly enhanced user convenience is an important advantage associated with the dosage form of this invention.

Progesterone formulated in the hydrogel forming dosage form can be used for transvaginal administration for the treatment of menopausal disorders (in combination with estrogen replacement therapy), menstrual irregularities, infertility due to inadequate luteal phase, and other disorders associated with progesterone deficiency. The concentration of progesterone may vary from 3 to 15, preferably from 4 to 10 percent by weight, based on the total weight of the dosage form. This dosage form can provide sustained release of progesterone resulting in therapeutic effectiveness for a period of 2 to 7 days. Marketed transvaginal formulations are currently available as cocobutter base suppositories or progesterone gelatin capsules. These formulations have the disadvantages of twice a day administration and local side effects of unacceptable vaginal discharges. Use of the highly biocompatible hydrogel forming progesterone dosage form can alleviate these problems and significantly improve patient convenience and compliance.

Other medicinal agents that can be used in the preparation of the compositions of this invention include, but are not limited to, those described in the above referenced J. R. Robinson patent (see especially col. 6, line 12 to col. 7, line 11). These agents are incorporated. herein, by reference. In addition chemotherapeutic agents such as 5-Fluorouracil and Mitomycin C may also be included.

Formulation of the pharmacologically active agent with the other components in accordance with this invention can be simply accomplished by dissolving all the components (for example the graft copolymer, water soluble plasticizer, and optionally compatible water soluble polymer) in a suitable solvent, such as acetone, chloroform, tetrahydrofuran, N,N-dimethylformamide, etc. and then isolating the formulated mixture by evaporating the solvent by heating under vacuum. Alternatively, all the components can be homogeneously mixed in the melt in a conventional processing equipment such as an extruder or a sigma blade mixer.

EXAMPLE 1

In a 1-liter resin kettle equipped with a stirrer, a thermometer, a condenser, and a nitrogen inlet tube, was placed 47.5 g. of N,N-dimethylacrylamide, 47.5 g. of acrylic acid, and 5.0 g. of polystyrene methacrylate macromonomer having a number average molecular weight of 12,000 (manufactured by Polymer Chemistry Innovations, Inc.), and 170 ml of ethyl acetate. A solution of 100 mg of azobisisobutyronitrile in 5.0 ml of ethyl acetate was slowly added to the mixture under constant stirring until a completely clear solution was obtained. The reaction mixture was heated to 50° C. and maintained at that temperature for a period of 1 hour under nitrogen atmosphere. The reaction mixture was then further heated and allowed to reflux for an additional period of 2 hours also under nitrogen atmosphere, after which time a viscous polymer solution was obtained. The resultant graft copolymer was precipitated by gradual addition of the solution to 1200 ml of diethyl ether under vigorous agitation. The precipitate was isolated by filtration, washed with excess diethyl ether, and dried at 50° C. under vacuum until free of solvent and residual monomer odor to yield 95 g. of the graft copolymer.

EXAMPLE 2

A solution of 10 g. of the graft copolymer, 15 g. of poly(N,N-dimethylacrylamide), 10 g. of polyethylene glycol, and 700 mg of clotrimazole in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick soft polymeric film containing 2% clotrimazole. The film upon equilibration in normal saline solution for a period of 24 hours formed a jelly like mass.

EXAMPLE 3

A solution of 10 g. of the graft copolymer, 15 g. of poly(N,N-dimethylacrylamide), 5.0 g. of polyethylene glycol, and 10.0 g of nonoxynol-9 in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick soft polymeric film containing 25% nonoxynol-9. The film upon equilibration in normal saline solution for a period of 24 hours formed a jelly like mass.

EXAMPLE 4

A solution of 10 g. of the graft copolymer, 15 g. of poly(N,N-dimethylacrylamide), 10 g. of polyethylene glycol, and 2.1 g. of progesterone in 200 ml of chloroform was obtained by stirring the mixture for a period of 24 hours. An aliquot of the solution was cast over a silicone coated release paper and dried in an air oven at 50° C. for a period of 2 hours to yield 60 square inches of 4 mil thick polymeric film containing 5.7% progesterone. The film upon equilibration in normal saline solution for a period of 24 hours formed a jelly like mass.

The mucoadhesive compositions of this invention may also contain conventional pharmaceutically acceptable excipients which are non-toxic, do not cause any irritation or inflammation of the mucosal membranes, and do not alter mucoadhesivity of the composition in an adverse manner.

2-Pyrrolidone, commercially available as Soluphor® from BASF Corporation, Mount Olive, N.J. is a particularly useful solvent for the preparation of solutions of the graft copolymer. These solutions have an interesting property in that they undergo in situ gelation in an aqueous environment such as that on the mucosal surfaces in the body. Therefore, the solution becomes a convenient method of dispensing the controlled release mucoadhesive composition to the tissue. The gelation process very likely involves exchange of 2-pyrrolidone with water, resulting in the formulation of a jelly like hydrogel. 2-pyrrolidone is highly advantageous for this purpose due to its relatively benign toxicological characteristics and excellent solubility properties. Hydrocolloid or water soluble polymers may be dispersed or dissolved in the above solutions, and may provide increased water absorption capacity, and may even enhance the mucosal adhesivity or the composition and its residence time (see examples 10 and 11).

The kinds of sustained release dosage forms that can be prepared from the formulations of the present invention include, but are not limited to, user friendly articles such as powders, capsules, suppositories, ointments, films, laminates, tablets, solutions, dispersions and the like. The mucoadhesive compositions may also be used as a coating on dosage forms such as tablets and suppositories. The methods of preparation of these dosage forms are commonly known in the field to those skilled in the art. Some of these methods of preparation have been described in the above referenced Robinson Patent. The dosage form may be in a dry, dehydrated state, or plasticized with a suitable plasticizer, or in a partially hydrated state.

The invention also envisions a method of treatment, which involves application of the controlled release composition to a mucosal tissue. The pharmaceutical composition gradually hydrates by sorption of tissue fluids at the application site to ultimately a very soft jelly like mass and exhibits adhesion to the mucosal surface. During the period of time the composition is adhered to the mucosal surface it provides sustained release of the pharmacologically active agent, which then is absorbed by the mucosal tissue. Administration of the composition to mucosal surfaces in the eye can be done, for example, by instilling a liquid formulation in to the cul-de-sac. The composition can be contacted with the mucosa of mouth, vagina, rectum or nose, by hand or other suitable applicator. The application of the composition to the mucosa of the gastrointestinal tract mucosal tissue may be carried out by swallowing the composition.

EXAMPLE 5

In a 500-ml 4-necked reaction flask, equipped with a stirrer, a thermometer, a condenser, and a nitrogen inlet tube, was placed 43.75 g. of N,N-dimethylacrylamide, 5.0 g. of acrylic acid, and 1.25 g. of polystyrene methacrylate macromonomer having a number average molecular weight of 12,000 (manufactured by Polymer Chemistry Innovations, Inc.), and 170 ml of acetone. A solution of 50 mg of azobisisobutyronitrile in 5.0 ml of acetone was slowly added to the mixture under constant stirring until a completely clear solution was obtained. The reaction mixture was heated to 50° C. and maintained at that temperature for a period of 1 hour under nitrogen atmosphere. The reaction mixture was then further heated and allowed to reflux for an additional period of 1 hour also under nitrogen atmosphere, after which time a viscous polymer solution was obtained. The resultant graft copolymer was precipitated by gradual addition of the solution to 1200 ml of diethyl ether under vigorous agitation. The precipitate was isolated by filtration, washed with excess diethyl ether under vacuum until free of odor to yield 45 g. of the polystyrene graft copolymer.

EXAMPLE 6

A 20 mil thick film of the graft copolymer plasticized with all equal weight of polyethylene glycol 400 was prepared by casting a solution of 5.0 g. of the graft copolymer, prepared in Example 5, and 5.0 g. of polyethylene glycol 400 in 50 ml of 1-methoxy-2-propanol, followed by evaporation of the solvent in a vacuum oven. A 1.3 g. sample of the film was placed in 6.1 ml of water in a small plastic beaker, which was covered with a polyethylene film, and allowed to stand overnight, by which time the film had absorbed all the water and formed a jelly like mass.

Mucoadhesivity of the graft copolymer was tested in terms of its shear resistance, between two surfaces of agar/mucin gel, utilized as an in vitro simulation of a mucosal surface. A sheet of agar/mucin gel (5% agar/5% porcine mucin) was prepared by first preparing a thick viscous paste of 5 g. of agar and 5 g. of mucin in 100 ml of boiling water, digesting the paste at this temperature for about 20 minutes, and then casting in a petri dish. Upon cooling overnight at room temperature, covered with a polyethylene film, a solid slippery sheet of the agar/mucin gel was obtained. Using the same procedure, an agar/mucin paste was cast into a small plastic holder, creating a an agar/mucin plug having a surface area of 1.8 square centimeters About 350 mg of the partially hydrated graft copolymer film was placed on the plug of agar/mucin gel. The combined weight of the plastic holder and the agar/mucin plug was 5.3 gms. The holder was then placed on the gel surface in the petri dish so that the hydrated graft copolymer film was sandwiched between two surfaces of agar/mucin gel. The petri dish was now placed in a vertical position in an incubator at 40° C. under 100% relative humidify environment. The period of time over which the hydrated graft copolymer stayed attached to the two agar/mucin surfaces, under a gravity, and with a load of 5.3 gms, was recorded. Similar measurements were made using the marketed products Gyne-Lotrimin®, (a negative control, non-mucoadhesive vaginal antifungal cream) and Replens® (a positive control, mucoadhesive containing long acting vaginal moisturizer). The graft copolymer stayed attached to the 5.3 gms plug for a period of more than 72 hours (at which point the test was discontinued), whereas both the marketed products failed within seconds to hold the plug. A cohesive failure mode was observed for both the marketed products.

EXAMPLE 7

In another similar experiment, the partially hydrated graft copolymer film of Example 6 was sandwiched between a two pieces of a freshly excised rabbit vaginal mucosa, one attached to agar/mucin gel in a petri dish and the other attached to the 5.3 g. agar/mucin plug. The graft copolymer gel exhibited adhesion to the vaginal mucosal surface and resisted dislodgment with a load of 5.3 g. under gravity for a period of 3–4 hours at 40° C. in a 100% relative humidity environment. Both Gyne-Lotrimin® and Replens® controls immediately failed under the same experimental conditions.

EXAMPLE 8

About 1 square centimeter piece of the polyethylene glycol 400 plasticized graft copolymer film, as prepared in Example 6, was attached to the buccal mucosa of a human volunteer. The film exhibited strong adhesion to the buccal mucosa, as manifested by its resistance to detachment by a peeling action.

EXAMPLE 9

A viscous solution of the graft copolymer, described in Example 5, was prepared by dissolving 13 g. of graft copolymer in 87 ml of 2-pyrrolidone. About 350 mg of the solution was placed on an agar/mucin gel and allowed to equilibrate for a period of 15 minutes by which time the solution had become jelly like mass. The 5.3 g. agar/mucin gel plug was then placed on the gel surface of the graft copolymer solution in the petri dish so that the graft copolymer gel was sandwiched between two surfaces of agar/mucin gel. The petri dish was now placed in a vertical position in an incubator at 40° C. under 100% relative humidity environment. The period of time over which the graft copolymer gel stayed attached to the two agar/mucin surface under a gravity, with a load 5.3 g., was recorded. The graft copolymer stayed attached to the 5.3 g. plug for a period of more than 72 hours, at which point the test was discontinued.

EXAMPLE 10

To 5.8 g. of the graft copolymer solution of Example 7 was added 60 mg of Poly(acrylic acid), having a molecular weight of 3,000,000. and thoroughly mixed with a spatula. In a sealed container the mixture was allowed to stand overnight, by which time it had become a homogeneous almost clear solution. About 300 mg of the thus formed solution was placed on a agar/mucin gel and allowed to equilibrate for a period of 15 minutes, by which time the solution had become a jelly like mass exhibiting strong adhesion to the agar mucin gel, as manifested by its resistance, to dislodgement upon manipulation with a spatula.

EXAMPLE 11

To 9.3 g of the graft copolymer solution of Example 7 was added 280 mg of sodium carboxymethyl cellulose, and thoroughly mixed with a spatula. In a sealed container the mixture was allowed to stand overnight, by which time it had become a homogeneous, almost clear solution. About 300 mg of the thus formed solution was placed on a agar/mucin gel and allowed to equilibrate for a period of 15 minutes, by which time the solution had become jelly like mass exhibiting strong adhesion to the agar mucin gel, is manifested by, its resistance to dislodgement upon manipulation with a spatula.

What is claimed is:

1. A mucoadhesive hydrophilic drug delivery system comprising:
   (A) a drug or a plurality of drugs to be delivered, and
   (B) a drug delivery vehicle consisting essentially of a thermoplastic graft copolymer, said graft copolymer being a reaction product of:
      (1) a polystyrene macromonomer having an ethylenically unsaturated functional group, and
      (2) at least one hydrophilic acidic monomer having an ethylenically unsaturated functional group,
   wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
   said graft copolymer being present in said drug delivery system in an amount sufficient to cause said drug delivery system to form a water swollen but insoluble jelly like mass upon contact with the biological environment.

2. A sustained release mucoadhesive hydrophilic drug delivery system comprising:

(A) a drug or a plurality of drugs to be delivered, and
(B) a drug delivery vehicle consisting essentially of a thermoplastic graft copolymer, said graft copolymer being a reaction product of:
  (1) a polystyrene macromonomer having an ethylenically unsaturated functional group, and
  (2) at least one hydrophilic acidic monomer having an ethylenically unsaturated functional group,
wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%, said graft copolymer being present in said drug delivery system in an amount sufficient to cause said drug delivery system to form a water swollen but insoluble jelly like mass upon contact with the biological environment.

3. A mucoadhesive hydrophilic drug delivery system as in claim 1 wherein the weight percent of the drug to be delivered is between 0.001 and 40.

4. A mucoadhesive hydrophilic drug delivery system as in claim 1 wherein the hydrophilic monomer further comprises a neutral monomer.

5. A mucoadhesive hydrophilic drug delivery system as in claim 1 wherein the hydrophilic monomer is acrylic acid.

6. A mucoadhesive hydrophilic drug delivery system as in claim 4 wherein the hydrophilic neutral monomer is N,N-dimethylacrylamide.

7. A mucoadhesive hydrophilic drug delivery system as in claim 1 in the form of powder.

8. A dispersion comprising a mucoadhesive hydrophilic drug delivery system as in claim 1, and any acceptable liquid pharmaceutical excipient.

9. A sustained release mucoadhesive hydrophilic drug delivery system as in claim 1 packaged in a unit dose.

10. A mucoadhesive hydrophilic drug delivery system as in claim 1 wherein the drug is a spermicide.

11. A mucoadhesive hydrophilic drug delivery system as in claim 1 wherein the spermicidal drug is Nonoxynol 9.

12. A mucoadhesive hydrophilic drug delivery system as in claim 1 wherein the drug is selected from the group consisting of: progesterone, estrogen, estradiol, and estriol.

13. A mucoadhesive hydrophilic drug delivery system as in claim 1 wherein the drug is an antifungal agent.

14. A mucoadhesive hydrophilic drug delivery system as in claim 13 wherein the drug is selected from the group consisting of: miconazole nitrate and clotrimazole.

15. A mucoadhesive hydrophilic drug delivery system as in claim 1 wherein the drug is a protein.

16. A mucoadhesive hydrophilic drug delivery system as in claim 1 wherein the drug is a peptide.

17. A mucoadhesive hydrophilic drug delivery system as in claim 1 wherein the drug is systemically absorbed and has therapeutic effectiveness in a distal part of the body.

18. A sustained release mucoadhesive hydrophilic drug delivery system comprising:
  (A) a drug or a plurality of drugs to be delivered, and
  (B) a drug delivery vehicle consisting essentially of a thermoplastic graft copolymer, said graft copolymer being a reaction product of:
    (1) a polystyrene macromonomer having an ethylenically unsaturated functional group, and
    (2) at least one hydrophilic acidic monomer having an ethylenically unsaturated functional group,
    (3) and a hydrophilic neutral monomer having an ethylenically unsaturated functional group,
wherein the weight percent of the polystyrene macromonomer in the graft copolymer is between about 1 and about 20%, and the weight percent of the total hydrophilic monomer in the graft copolymer is between 80 and 99%, wherein at least about 10% of said total hydrophilic monomer is acidic, said graft copolymer when fully hydrated having an equilibrium water content of at least 90%,
  (C) a plasticizer
said graft copolymer being present in said drug delivery system in an amount sufficient to cause said drug delivery system to form a water swollen but insoluble jelly like mass upon contact with the biological environment.

19. A sustained release mucoadhesive hydrophilic drug delivery system as in claim 18 wherein the plasticizer is polyethylene glycol.

20. A composition comprising the sustained release mucoadhesive hydrophilic drug delivery system as in claim 18 further comprising at least one compatible hydrophilic polymer.

21. The mucosal drug delivery system as in claim 1, wherein the dosage form is a viscous solution.

* * * * *